(12) United States Patent
Groenendijk et al.

(10) Patent No.: US 9,968,629 B2
(45) Date of Patent: May 15, 2018

(54) PRODUCT AND METHOD FOR SUPPORTING URIDINE HOMEOSTASIS

(71) Applicant: N.V. Nutricia, Zoetermeer (NL)

(72) Inventors: Martine Groenendijk, Utrecht (NL); Robert Johan Joseph Hageman, Utrecht (NL); Mattheus Cornelis De Wilde, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 373 days.

(21) Appl. No.: 14/421,432

(22) PCT Filed: Aug. 13, 2013

(86) PCT No.: PCT/NL2013/050595
§ 371 (c)(1),
(2) Date: Feb. 12, 2015

(87) PCT Pub. No.: WO2014/027885
PCT Pub. Date: Feb. 20, 2014

(65) Prior Publication Data
US 2015/0297622 A1    Oct. 22, 2015

(30) Foreign Application Priority Data

Aug. 13, 2012  (WO) ................ PCT/NL2012/050561

(51) Int. Cl.
| | | |
|---|---|---|
| *A61K 31/7072* | (2006.01) | |
| *A61K 31/202* | (2006.01) | |
| *A61K 31/4415* | (2006.01) | |
| *A61K 31/14* | (2006.01) | |
| *A61K 31/66* | (2006.01) | |
| *A61K 33/30* | (2006.01) | |
| *A61K 33/06* | (2006.01) | |
| *A61K 31/714* | (2006.01) | |
| *A61K 31/519* | (2006.01) | |
| *A61K 45/06* | (2006.01) | |
| *A61K 31/685* | (2006.01) | |

(52) U.S. Cl.
CPC .......... *A61K 31/7072* (2013.01); *A61K 31/14* (2013.01); *A61K 31/202* (2013.01); *A61K 31/4415* (2013.01); *A61K 31/519* (2013.01); *A61K 31/66* (2013.01); *A61K 31/685* (2013.01); *A61K 31/714* (2013.01); *A61K 33/06* (2013.01); *A61K 33/30* (2013.01); *A61K 45/06* (2013.01)

(58) Field of Classification Search
CPC .................................................. A61K 31/7072
See application file for complete search history.

(56) References Cited

U.S. PATENT DOCUMENTS 5,567,689 A    10/1996    Sommadossi et al.

FOREIGN PATENT DOCUMENTS

| WO | WO-00/06174 | 2/2000 |
| WO | WO-2007/089703 A2 | 8/2007 |
| WO | WO-2009/002146 A1 | 12/2008 |

OTHER PUBLICATIONS

Yamamoto et al., Clinica Chimica Acta, 2011, 412, p. 1712-1724.*
Van Groeningen et al., J. Natl. Cancer Inst., 1991, 83, p. 437-441. (Year: 1991).*
Cao, et al. "Abnormalities in Uridine Homeostatic Regulation and Pyrimidine Nucelotide Metabolism as a Consequence of the Deletion of the Uridine Phosphorylase Gene", The Journal of Biological Chemistry (Jun. 3, 2005), vol. 280, No. 22, 21169-21175.
Safarjalani, et al. "Enhancement of the bioavailability of oral uridine by coadministration of 5-(phenylthio)acyclouridine, a uridine phosphorylase inhibitor: implications for uridine rescue regimens in chemotherapy", Cancer Chemother Pharmacol (Nov. 2001), vol. 48, No. 5, pp. 389-397.
International Search Report of PCT/NL2013/050595 dated Sep. 26, 2013.

* cited by examiner

*Primary Examiner* — Jonathan S Lau
(74) *Attorney, Agent, or Firm* — Gilberto M. Villacorta; Sunit Talapatra; Foley & Lardner LLP

(57) ABSTRACT

This invention pertains to the use of an uridine source, preferably uridine monophosphate, for increasing, controlling and/or maintaining fasting plasma uridine concentrations in a range of 4 to 8 μM in a subject in need thereof, comprising administering to said subject a composition comprising 300-900 mg of said uridine source daily for a period of at least 4 weeks. In particular, the use of an uridine source is intended forelderly and/or subjects suffering from neurological disorders such as Alzheimer's Disease and dementia syndromes.

25 Claims, 1 Drawing Sheet

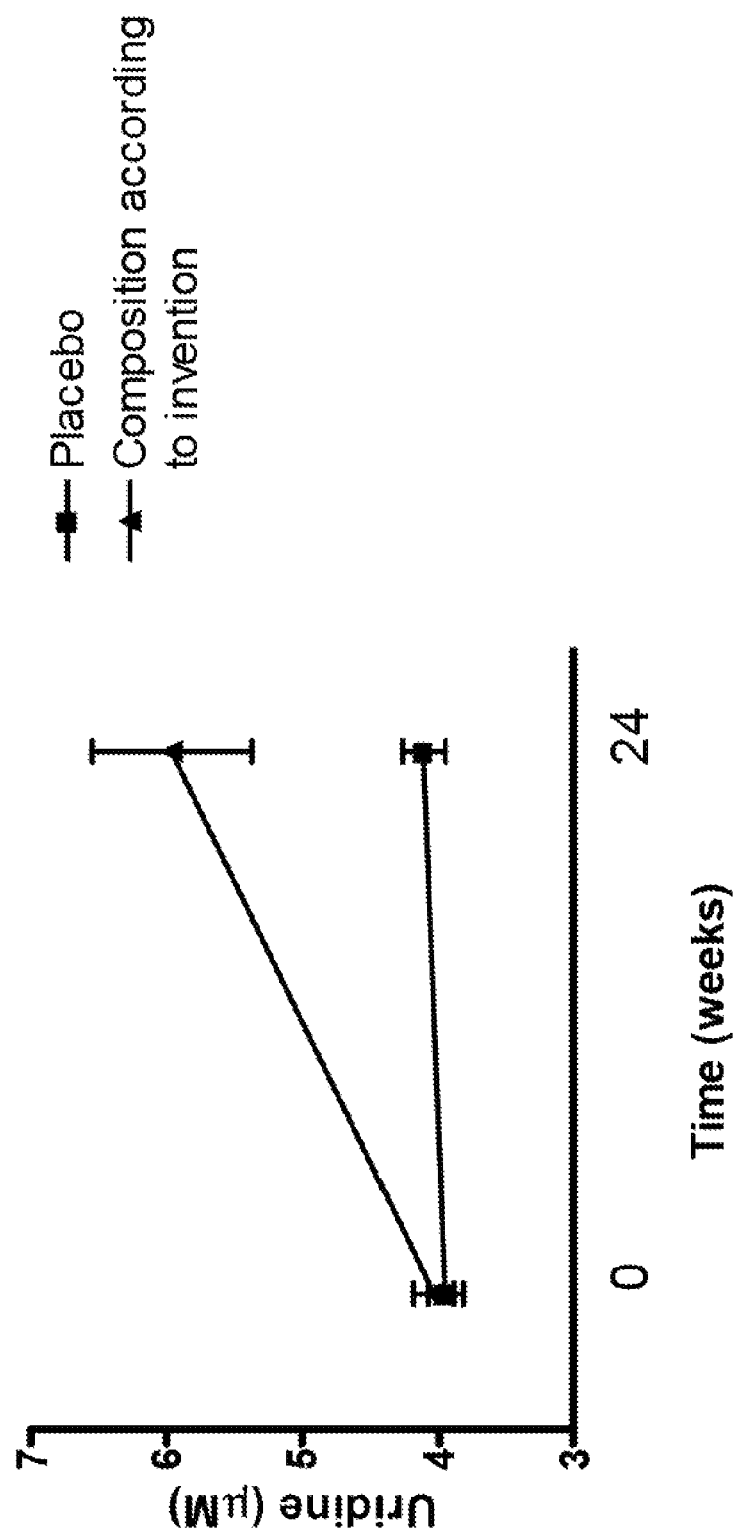

PRODUCT AND METHOD FOR SUPPORTING URIDINE HOMEOSTASIS

CROSS REFERENCE TO RELATED APPLICATIONS

The present application is a National Stage of International Application No. PCT/NL2013/050595 filed on Aug. 13, 2013, which was published on Feb. 20, 2014, as WO 2014/027885 A1; and claims the benefit of International Application No. PCT/NL2012/050561 filed Aug. 13, 2012, the entire disclosures of which are incorporated herein by reference.

FIELD OF THE INVENTION

The invention is in the field of uridine homeostasis, and particularly relates to maintaining plasma uridine concentrations at physiologically beneficial levels, in subjects in need thereof, particularly elderly and/or subjects suffering from neurological disorders such as Alzheimer's Disease and dementia syndromes.

BACKGROUND OF THE INVENTION

Uridine and its metabolites play a crucial role in a number of important metabolic pathways such as the synthesis of DNA and RNA, of β-alanine, but also the synthesis of membrane phospholipids (PLs), known to be decreased in the brains of Alzheimer's disease (AD) patients. PLs are synthesized e.g. through the Kennedy pathway. Uridine, docosahexaenoic acid (DHA) and choline are involved to form the PL phosphatidylcholine (PC). The enzymes catalyzing the formation of PC are not saturated at physiological conditions in humans and therefore increased blood levels of these nutrients will increase the overall rate of PC biosynthesis.

WO 00/06174 relates to the treatment of neurological disorders such as Alzheimer's disease and other dementia syndromes where exogenous uridine or a uridine source is administered in dosages broadly ranging between 10 mg and 10 gram per day, in order to increase brain cytidine levels. There is no report of uridine plasma concentrations measured.

It is generally known that uridine is heavily metabolized in the human body. Though it is metabolized in most cells, the liver appears to determine the uridine plasma concentrations to a great extent. Uridine is the main metabolite for inter-organ transport of uridine moieties and a constant high plasma concentration ensures ample supply of uridine for peripheral uridine use and metabolism. Therefore under normal physiological conditions uridine is often found present in blood of different species in relatively high and constant concentrations (1-5 µM), but its half time in the plasma is approximately 3-4 hours. This is indeed found in WO 2007/089703, disclosing medicaments comprising 200 mg-1 gram uridine or 300-1.2 g uridine monophosphate (UMP) for treating and ameliorating age-associated memory impairment, memory disorders and brain damage. FIG. 3 in WO 2007/089703 shows a fast decay in plasma uridine levels; after 6-8 hours all administered uridine has been used or is catabolised. It can be derived from FIG. 3 that there is no long-term effect expected from increasing dosages. Furthermore, the use of high doses of uridine is hampered by its toxic side effects including phlebitis, pyrogenic reactions and diarrhea.

These drawbacks are further discussed in U.S. Pat. No. 5,567,689 which rather seeks the solution in co-administering compounds that inhibit renal clearance of uridine, such as dilazep and hexobendine. Safarjalani (Cancer Chemother Pharmacol. 2001 November; 48(5):389-97) teaches likewise, co-administering together with the uridine source an inhibitor of uridine phosphorylase which is known to catabolise uridine to uracil, which can be cleared from the plasma compartment. However, these inhibitors complicate administration protocols, but also demand a careful design per patient in order to induce plasma values between 4.5 and 6 µM As demonstrated by Cao et al. (J. Biol. Chem, 10; 1074; 2005), blockade of uridine phosphorylase can readily increase plasma uridine concentrations several-fold. In addition the phosphorylase inhibitors also demonstrate several specific and adverse systemic effects.

Some authors take yet a different path for increasing half-life by derivatization of the uridine source. Still it requires increased dosages and also repeated daily dosages.

The inventors have therefore concluded that there remains a need for increasing and/or maintaining uridine plasma at physiologically acceptable and/or healthy levels without the disadvantages discussed above. There is also a need for prolonging the increased and/or maintained uridine plasma levels for extended time intervals.

SUMMARY OF THE INVENTION

From data on plasma uridine levels for elderly collected by the inventors together with isolated values obtained in clinical trials with different populations scattered all over the prior art, the inventors found that there is in fact a significant difference in plasma uridine level between healthy persons (in particular not older than 55 years), and elderly (i.e. older than 60 years); and an even more significant difference in plasma uridine level between healthy persons and AD patients. These data indicate that plasma uridine, a necessary precursor for PC formation, varies with the health status of a subject. The decrease of uridine levels may occur in situations demanding increased PC formation to compensate for the increased loss of membrane PLs, such as observed in AD.

Based on these observations, the inventors conclude there is a particular need for achieving long-term lasting uridine plasma concentrations, preferably at about 4 to about 8 µM, more preferably at about 4.5 to about 7 µM, even more preferably about 4.5 to about 6 µM, in elderly and/or a subject in need thereof, such as a patient at risk of or suffering from a pathological brain dysfunction, in particular (preferably) a cognitive disorder or a memory disorder, and more preferably (at risk of or) suffering from a neurodegenerative disease. This is particularly important because these target groups are susceptible of age-associated memory and/or cognitive disorders.

It is thus an object of the invention to increase, maintain and/or prolong uridine plasma levels within physiologically acceptable ranges, preferably at about 4 to about 8 µM, more preferably at about 4.5 to about 7 µM, even more preferably about 4.5 to about 6 µM, in subjects in need thereof, particularly in elderly and/or in a subject at risk of or suffering from a pathological brain dysfunction, in particular suffering from a cognitive disorder and/or a memory disorder, and preferably at risk of or suffering from a neurodegenerative disease.

It is also an object to maintain uridine levels within acceptable concentrations and avoid increased renal clearance. It is also an object to avoid the need for uridine phosphorylase inhibitors, uridine secretion inhibitors and compounds which compete with uridine in renal transport mechanisms. It is also an object to maintain uridine plasma concentrations in a range of about 4 to about 8 μM, preferably at about 4.5 to about 7 μM, more preferably about 4.5 to about 6 μM.

The inventors have found that the oral administration of 300-900 mg of a uridine source, optionally combined with other food components, increases, controls and/or maintains fasting plasma uridine concentrations in a range of 4 to 8 μM in elderly individuals in need thereof.

These insights are unprecedented and render it possible to sufficiently maintain uridine concentrations overall without the need for high dosages, or with relatively short dosage regimen, contrary to beliefs in the art.

Preferably no drug is added to the composition, in particular no drug providing any uridine phosphorylase inhibitor, any uridine secretion inhibitor or any compound competing with uridine in renal transport mechanisms.

One object of the invention is thus the use of an uridine source in the manufacture of a composition for increasing, controlling and/or maintaining fasting plasma uridine concentrations in a range of 4 to 8 μM in a subject in need thereof, comprising administering to said subject a composition comprising 300-900 mg of said uridine source (based on UMP equivalents), daily, for a period of at least 4 weeks.

In the context of the present invention, fasting plasma uridine concentration in a range (substantially) outside that of 4 to 8 μM in a subject is considered abnormal.

One object of the invention is thus a uridine source, preferably uridine or a phosphate thereof, more preferably a phosphate thereof, even more preferably UMP, for use in the manufacture of a composition for increasing and maintaining fasting plasma uridine concentration in a range of about 4 to about 8 μM, preferably in a range of about 4.5 to about 7 μM, more preferably in a range of about 4.5 to about 6 μM, in a subject in need thereof, preferably a subject suffering from a pathological brain dysfunction, preferably a neurodegenerative disease, more preferably AD, comprising administering to said subject a composition comprising 300-900 mg of said uridine source daily for a period of at least 4 weeks, preferably at least 6 weeks.

Preferably, the compliance (i.e. the degree to which the subject correctly follows the dosage regimen) should be higher than 70%, preferably higher than 80%, more preferably higher than 90%, even more preferably higher than 95%, over said period of at least 4 weeks, preferably of at least 6 weeks.

An object of the invention is thus a uridine source, preferably uridine or a phosphate thereof, more preferably a phosphate thereof, even more preferably UMP, for use in the treatment or prevention of a pathological brain dysfunction, preferably of a neurodegenerative disease, more preferably AD, wherein the uridine source is administered for a period of weeks, preferably at least 4 weeks, more preferably at least 6 weeks, discontinued for a period of days, preferably less than 2 weeks, more preferably less than 1 week.

One object of the invention is a uridine source, preferably uridine or a phosphate thereof, more preferably a phosphate thereof, even more preferably UMP, for use in the prevention or treatment of a pathological brain dysfunction, preferably a neurodegenerative disease, for administering to a subject in need thereof, (so as to reach and sustain the plasma uridine basal level of said subject in a range of about 4 to about 8 μM), wherein the administration pattern comprises administering a therapeutically effective amount of said uridine source to the subject that is continuous, i.e. at least once a day consecutively over a period of weeks, such as 4, 5, preferably over a period of at least 6 weeks, more preferably over a period of 12, 13, 14, 15, 20 weeks, even more preferably over a period of 24 weeks or more, then discontinuing said administration by means of a continual lack of treatment for consecutive days over a period of days, such as 2, 3, 4, 5, or 6 days, preferably over a period of less than 2 weeks, preferably over a period of 1 week, and repeating this pattern of administration and discontinuance of administration for as long as necessary.

Alternatively, the discontinuance of said administration can be by means of a reduced amount of said uridine source, such as a reduction of 25% to 90%, preferably a reduction of 50% to 75% compared to the treatment dosage (e.g. compared to the first composition), or such as less than 300 mg daily, for as long as necessary, preferably for consecutive days, or weeks, or months, or even years, and repeating this pattern of administration and discontinuance of administration (for as long as necessary). The second composition is administered for as long as necessary, preferably for consecutive days, preferably weeks (such as at least 2, 3, 4, 5, 6, 12, 24 or 52 weeks), preferably months (such as at least 10, 11, 12, 24, or more months), or even years (such as at least 2, 3, 4, 5, 7, 7, 8, 9 or 10 years).

The discontinuance of said administration can be by means of a reduction of the compliance such as a compliance lower than 70%, or lower than 60%, even lower than 50%. In particular, the discontinuance of said administration can be by means of administration of the first composition or of the second composition every other day, or every two days, or every 3 days.

These dosage regimens not only are convenient to the subject in need for increasing, controlling and/or maintaining fasting plasma uridine concentrations but also increase compliance, in particular when said first composition and possibly said second composition is administered only once a day.

FIGURES

The FIGURE shows the effect of administering a uridine source on basal plasma uridine levels in AD patients. Plasma uridine was measured in AD patients before intake of a placebo or an uridine enriched product and 24 weeks after daily consumption of these. Plasma samples were taken in overnight fasted patients and at 24 weeks, approximately 24 hours after the last consumption of the placebo or the composition comprising said uridine source.

DETAILED DESCRIPTION

Based on these observations unprecedented in the art, the invention in one aspect pertains to a method for increasing, controlling and/or maintaining fasting plasma uridine concentrations, preferably in a range of about 4 to about 8 μM, more preferably in a range of about 4.5 to about 7 μM, even more preferably in a range of about 4.5 to about 6 μM, in a subject in need thereof, said method comprising administering to said subject a composition comprising a daily dose of 300-900 mg of a uridine source, for a period of at least 4 weeks, preferably at least 6 weeks.

Worded differently, the invention relates to the use of an uridine source in the manufacture of a composition for increasing, controlling and/or maintaining fasting plasma uridine concentrations, preferably in a range of about 4 to about 8 μM, more preferably in a range of about 4.5 to about 7 μM, even more preferably in a range of about 4.5 to about 6 µM, in a subject in need thereof, comprising administering to said subject a composition comprising a daily dose of 300-900 mg of said uridine source for a period of at least 4 weeks, preferably at least 6 weeks. The ranges are carefully selected; both lower and higher concentrations are believed to relate to pathologies. The preferred route of administration is enteral, most preferably oral.

In the context of the invention, 'fasting' plasma uridine concentrations are defined as the plasma uridine concentrations as these are determined after at least 9 hours, preferably at least 12 hours, more preferably at least 14 hours, preferably after a period of 9 to 24 hours, more preferably after a period of 14 to 24 hours following the administration according to the invention of a composition, food or supplement or a pharmaceutical product comprising a source of uridine, most preferably a composition comprising a uridine source as defined herein. It may also be referred to as the 'post-absorptive state' and clearly distinguishes from the postprandial states after ingestion of an uridine source.

For measuring the fasting plasma uridine level, the blood sample of the subject is preferably collected at least 9 hours, more preferably at least 14 hours after the last administration according to the invention of said composition, and after a period in which no significant uridine source was administered to the subject, i.e. no more than in a normal diet, i.e. less than 100 mg, even less than 50 mg for a normal diet over said 9 or 14 hours.

During the period of time during which administration of the uridine source is discontinued (stopped or preferably reduced), the fasting plasma uridine concentrations may be determined many hours, in particular 24 h or more, even days, after the last administration of a uridine source according to the invention.

The plasma uridine concentrations can be measured using any of the methods well known in the art (e.g. as provided in the example section).

Related therewith, a further aspect the invention pertains to the use of an uridine source in the manufacture of a composition for controlling and/or maintaining plasma uridine concentrations in a range of about 4 to about 8 µM, preferably in a range of about 4.5 to about 7 µM, more preferably in a range of about 4.5 to about 6 µM in a subject in need thereof, comprising administering to said subject a composition comprising 300-900 mg of said uridine source daily for at least 4 weeks. Worded differently, the invention also pertains to a method for controlling and/or maintaining plasma uridine concentrations in a range of about 4 to about 8 µM, preferably in a range of about 4.5 to about 7 µM, more preferably in a range of about 4.5 to about 6 µM in a subject in need thereof, comprising administering to said subject a composition comprising 300-900 mg of said uridine source daily for at least 4 weeks. The plasma uridine levels can thus be controlled and maintained at physiologically acceptable levels for a period of days, preferably at least 1 week, more preferably at least 2 weeks, starting from the day after the above treatment/administration ends.

The treatment preferably involves daily administration of the product for at least 4 weeks, preferably for at least 6 weeks. The product is preferably administered (preferably daily) for at least 7 weeks, more preferably at least 8 weeks, more preferably at least 9 weeks, more preferably at least 10 weeks, most preferably at least 11 weeks, particularly at least 12 weeks, more particularly at least 24 weeks. The treatment preferably involves daily administration of the product once a day. An advantage of a daily administration only once a day lies in the compliance improvement.

In a further aspect, the invention pertains to the above use or a method, said use or method comprising administering (in a first treatment phase, or first dosage regimen) a first composition comprising about 300-900 mg of a uridine source daily for at least 4 weeks, preferably at least 6 weeks, subsequently (in a second treatment phase, or second dosage regimen) administering a second composition comprising substantially less of a uridine source than the first composition administered, preferably 25% to 90% less, more preferably 50% to 75% less, preferably on a daily basis.

The amount of said uridine source in the second composition is preferably at least 150 mg, and lower than the amount in the first composition, preferably comprised between a daily dose of 150 mg and 300 mg. Unless indicated otherwise, throughout the description, the first and the second composition in terms of all other properties, ingredients and amounts thereof are regarded indifferent; both are referred to as 'the product' or 'the composition'. Where specific reference to the second composition is made here below, it will conveniently be referred to as the low-uridine composition'. Once the treated subject demonstrates a (relatively) stable and desirable concentration of uridine in blood, such as comprised between about 4 and about 8 µM, preferably in a range of about 4.5 to about 7 µM, more preferably in a range of about 4.5 to about 6 µM, the subject may suitably enter a second phase of the treatment.

This moment of evaluation for entering the second phase will typically be after 4 weeks, preferably after 12 weeks, more preferably after 24 weeks after start of the first-phase-treatment, or preferably after 12 to 52 weeks after start of the first-phase-treatment, preferably between 20 and 30 weeks.

This second phase preferably starts immediately after, preferably the day after, the end of the first phase, though a discontinuance (by interruption) for a period of days, preferably up to one week, can be observed. The second phase (or second dosage regimen) can be continued for a period of days, weeks, months, or even years, before possibly entering the first treatment phase again.

In the second phase, the second composition is administered for as long as necessary, preferably for consecutive weeks (such as at least 2, 3, 4, 5, 6, 12, 24 or 52 weeks), preferably months (such as at least 10, 11, 12, 24, or more months), or even years (such as at least 2, 3, 4, 5, 7, 7, 8, 9 or 10 years).

The method or use of the invention comprises administering the composition comprising the aforementioned ingredients, and as further outlined below, to a subject in need thereof. The prophylactic or preventive aspect includes reducing the risk of occurring of disorders associated with uridine deficits, such as pathological brain dysfunction, in particular a cognitive disorder or a memory disorder, and preferably a neurodegenerative disease.

An aspect of the invention is to provide the use of a uridine source, as described herein, for the treatment and/or prevention of a pathological brain dysfunction, in particular a cognitive disorder or a memory disorder, and preferably a neurodegenerative disease, or a method for the same, comprising:

(i) a first dosage regimen, wherein a composition comprising a daily dose of 300-900 mg of an uridine source, based on UMP equivalents, preferably 400-800 mg, more preferably 500-700 mg, is administered, preferably for a period at least 4 weeks, preferably for at least 6 weeks, preferably for 12 to 52 weeks, more preferably 12 to 30 weeks, even more preferably 20 to 30 weeks, most preferably about 24 weeks; and (ii) optionally a second dosage regimen, wherein a second composition comprising substantially less uridine is administered, wherein the second composition preferably comprises:
  (a) an uridine source in an amount of at least 20% lower than the amount of the uridine source in the composition used in the first dosage regimen, more preferably 25% to 90% lower, even more preferably 50% to 75% lower; or
  (b) an uridine source in an amount of at least a factor 1.3 lower than the amount of the uridine source in the composition used in the first dosage regimen, more preferably between a factor 1.5 and a factor 10 lower, even more preferably between a factor 2 and a factor 3 lower; or
  (c) an uridine source in an amount of a daily dose of 75 mg-750 mg, based on UMP equivalents, preferably 100 mg-500 mg, more preferably 150-300 mg,
  provided that the amount or the dose of the uridine source is lower in the composition used in the second dosage regimen than in the composition used in the first regimen.

Preferably, the second dosage regimen is included in the use or the method according to this aspect of the invention. Preferably, the second dosage regimen comprises administration of said second composition for as long as necessary, preferably for consecutive days, preferably weeks (such as at least 2, 3, 4, 5, 6, 12, 24 or 52 weeks), preferably months (such as at least 10, 11, 12, 24, or more months), or even years (such as at least 2, 3, 4, 5, 7, 7, 8, 9 or 10 years). The second dosage regimen may be regarded as a discontinuance of the administration of the uridine source. In a preferred embodiment, the first dosage regimen is repeated after the second dosage regimen, as such creating a repeating pattern of uridine administration and discontinuance of uridine administration.

Alternatively, the discontinuance of said administration can be by means of administration of the first composition or of the second composition every other day, or every two days, or every 3 days.

The subject in need thereof is preferably a mammal, more preferably a human being. The above use or method is particularly suited for elderly. The term 'elderly' as used in the present invention means people aged 60 years and older, preferably people of at least 65 years of age.

More preferably, a subject in need thereof is a patient suffering from or at risk for a pathological brain dysfunction, in particular (preferably) as can be determined by applying recognized functional tests for measuring the different domains of brain function such as memory, cognition, verbal fluency, decision making planning and the like.

These domains can be combined in tests like MMSE for mild forms of cognitive impairment, episodic memory tests, more specifically episodic memory recall tests for very early/mild stages of cognitive impairments, and the Clinical Dementia Rating Scale and the ADAS-cog test for more mild to moderate, or more severe cases. Alternatively, pathology in the brain can be determined by measuring biomarkers in tissue (for example blood or cerebrospinal fluid (=CSF)). Examples of such biomarkers are the amount of abeta-42 and/or Tau protein in CSF, and/or the ratio of Tau protein to phosphorylated Tau protein.

Alternatively imaging techniques can be used for identifying brain atrophy or deposits of protein agglomerates, like Lewy bodies or amyloid plaques. For example applying positron emission topography with Pittsburgh compound B identifies amyloid deposits. The brain dysfunction can be caused by one or more of a variety of reasons including old age, tauopathies, amyloid-associated events, synucleopathies, impaired cerebrovascular functioning and general metabolic dysfunction like insulin-resistance and during metabolic syndrome.

In a preferred embodiment, the subject in need thereof is a human being that suffers from (or is at risk of) a neurodegenerative disorder. In particular, the subject is a human being that suffers from (or is at risk of) a memory and/or cognitive disorder, memory decline and/or cognitive dysfunction, such as Age Associated Memory Impairment (AAMI); Alzheimer's Disease; Parkinson's disease; Pick's disease; and/or dementia, including vascular dementia, frontotemporal dementia, semantic dementia or dementia with Lewy bodies, and Mild Cognitive Impairment (MCI). More particularly, the subject is a human being that suffers from (or is at risk of) Alzheimer's Disease. In the aforementioned conditions, memory and cognition functions are known to deteriorate in time.

In one preferred embodiment, the subject in need thereof is a human being that suffers from (or is at risk of) a memory and/or cognitive disorder, or memory decline and/or cognitive dysfunction. The subject is preferably suffering from memory and/or cognitive dysfunction associated with Alzheimer's disease [AD], Pick's disease, Lewy Body disease, Huntington's disease, or 'dementia syndrome'. Dementia syndrome encompasses vascular dementia, frontotemporal dementia and semantic dementia. The subject possibly does not suffer from any clinical stages associated with impaired functional connectivity yet.

Preferably, the subject in need thereof does not suffer from autism.

Uridine Source

For an uridine source, the present composition comprises uridine, and/or an equivalent thereof, including salts, phosphates, acyl derivatives and/or esters of uridine.

In terms of uridine source, the composition preferably comprises at least one of uridine (i.e. ribosyl uracil) and/or an equivalent thereof selected from the group consisting of deoxyuridine (deoxyribosyl uracil), uridine phosphates (e.g. UMP, dUMP, UDP, UTP), nucleobase uracil and acylated uridine derivatives, including triacetyluridine. Preferably, the composition to be administered according to the present invention comprises a source of uridine selected from the group consisting of uridine, deoxyuridine, uridine phosphates, uracil, and acylated uridine.

Preferably, the present composition comprises a uridine phosphate selected from the group consisting of uridine monophosphate (UMP), uridine diphosphate (UDP) and uridine triphosphate (UTP). Most preferably the present composition comprises UMP. Preferably at least 30 weight % of the uridine source in the present composition is provided by UMP, more preferably at least 50 weight %, more preferably at least 75 weight %, most preferably at least 95 weight %, based on the total weight of the uridine source in the composition.

Doses to be administered are given as "UMP equivalents". The amount of the other uridine sources correspond to the molar amount of UMP, which can be calculated from the molecular weight of UMP of 324 Dalton. Thus, 300-900 mg UMP corresponds to 0.9-2.8 mmol UMP.

The present method preferably comprises the administration of uridine source (the cumulative amount of uridine, deoxyuridine, uridine phosphates, nucleobase uracil and acylated uridine derivatives) in an amount of about 300-900 mg per day, preferably about 400-800 mg per day, more preferably about 500-700 mg per day. The present method preferably comprises the administration of a composition comprising about 300-900 mg UMP per 100 ml liquid product, preferably about 350-800 mg UMP per 100 ml liquid product, more preferably about 450-700 mg UMP per 100 ml liquid product.

In those aspects of the invention in which a first uridine dosage regimen is followed up by administration of a second dosage regimen or low-uridine composition comprising an uridine source at lower dosages, the above numbers apply to the first composition detailed here above. For the low-uridine composition already described above, the amount of the uridine source is preferably at least a factor 1.3 lower than the amount of the uridine source in the first composition administered, more preferably between a factor 2 and a factor 10 lower than the amount in the first composition administered, even more preferably between a factor 2 to a factor 3 lower than the amount in the first composition administered. Using the information above, the (preferred) ranges for the amount of the uridine source in the low-uridine composition can readily be calculated.

Preferably, the present composition comprises uridine phosphate, preferably uridine monophosphate (UMP).

The composition preferably does not contain any uridine phosphorylase inhibitors and uridine secretion inhibitors.

Product

Throughout the application, the terms 'product' and 'composition' are used interchangeably and account for the combination of ingredients—including the above uridine source-administered to a subject in need thereof. The 'product' and 'composition' refer to both the 'first' and 'second' composition, with the proviso that the amount of the uridine source in the 'second' composition is lower than that of the first composition administered to the subject as detailed above.

In one aspect of the present invention, the composition according to the invention may be used as a pharmaceutical product comprising one or more pharmaceutically acceptable carrier materials.

In another aspect of the present invention, the composition according to the invention may be used as a nutritional product, for example as a nutritional supplement, e.g., as an additive to a normal diet, as a fortifier, to add to a normal diet, or as a complete nutrition.

The pharmaceutical product, preferably for enteral application, may be a solid or liquid galenical formulation. Examples of solid galenical formulations are tablets, capsules (e.g. hard or soft shell gelatine capsules), pills, sachets, powders, granules and the like which contain the active ingredient together with conventional galenical carriers. Any conventional carrier material can be utilized. The carrier material can be organic or inorganic inert carrier material suitable for oral administration. Suitable carriers include water, gelatine, gum Arabic, lactose, starch, magnesium stearate, talc, vegetable oils, and the like. Additionally, additives such as flavoring agents, preservatives, stabilizers, emulsifying agents, buffers and the like may be added in accordance with accepted practices of pharmaceutical compounding. While the individual active ingredients are suitably administered in a single composition, they may also be administered in individual dosage units.

In one embodiment, the first and second compositions are identical in all other aspects.

In one embodiment, said second composition comprises the same nutrients as the first, preferably in an amount ranging from 0.1 to 2 times the RDA (recommended dietary allowance) levels. Preferably, for choline, the amount (in particular the daily dose) provided in said second product is 0.2 to 1.2 time the amount of the first composition. Preferably, for phospholipids, the amount (in particular the daily dose) provided in said second product is 0.4 to 2 times the amount of the first composition. Preferably, for fatty acids (in particular LC-PUFAs), the amount (in particular the daily dose) provided in said second product is 0.1 to 1 time the amount of the first composition.

Hence, the invention further relates to a kit of parts comprising i) one or more of uridine salts, phosphates, acyl derivatives or esters thereof; and ii) a lipid fraction comprising at least one of docosahexaenoic acid (22:6; DHA), eicosapentaenoic acid (20:5; EPA) and docosapentaenoic acid (22:5; DPA), or esters thereof, for the aforementioned use or for use in the aforementioned method.

In one embodiment, it is preferred to include iii) folic acid
In one embodiment, it is preferred to include iv) choline, or salts or esters thereof.

Preferably the composition comprising (i) and (ii)—and possibly (iii) and/or possibly (iv)—further comprises one or more of: phospholipids, vitamin E, vitamin C, selenium, vitamin B12, and vitamin B6.

Preferably the composition comprising (i) and (ii)—and possibly (iii) and/or possibly (iv)—further comprises minerals, in particular magnesium and/or zinc.

More preferably the kit of parts comprises a uridine source (preferably UMP), DHA, EPA, phospholipids, choline, vitamin E, vitamin C, selenium, vitamin B12, vitamin B6, folic acid, magnesium and zinc.

If the composition is a pharmaceutical product, such product may contain the daily dosage in one or more dosage units. The dosage unit may be in a liquid form or in a solid form, wherein in the latter case the daily dosage may be provided by one or more solid dosage units, e.g. in one or more capsules or tablets.

In another aspect of the present invention, the composition according to the invention may be used in a nutritional product comprising at least one component selected from the group of fats, proteins, and carbohydrates. It is understood that a nutritional product differs from a pharmaceutical product by the presence of nutrients which provide nutrition to the subject to which the composition is administered, in particular the presence of protein, fat, digestible carbohydrates and dietary fibers. It may further contain ingredients such as minerals, vitamins, organic acids, and flavoring agents. Although the term "nutraceutical product" is often used in literature, it denotes a nutritional product with a pharmaceutical component or pharmaceutical purpose. Hence, the nutritional composition according to the invention may also be used in a nutraceutical product.

The product of the invention is an enteral composition, preferably intended for oral administration. It is preferably administered in liquid form. In one embodiment, the product comprises a lipid fraction and at least one of carbohydrates and proteins, wherein the lipid composition provides between 20 and 50 en % of the total energy content of the food product. Herein 'en %' is short for energy percentage, which are calculated using the calculation factors 9 kcal per g lipid, 4 kcal per g protein or g digestible carbohydrates, 2 kcal per g dietary fibers and zero kcal for the other components in the composition. In one embodiment, the food product is a liquid composition containing between 0.8 and 1.4 kcal per ml.

Preferably the composition comprises (i) one or more of uridine, salts, phosphates, acyl derivatives or esters thereof; and (ii) a lipid fraction comprising at least one of docosahexaenoic acid (22:6; DHA), eicosapentaenoic acid (20:5; EPA) and docosapentaenoic acid (22:5; DPA), or esters thereof, for the aforementioned use or for use in the aforementioned method Preferably the composition comprising (i) and (ii) further comprises folic acid.

Preferably the composition comprising (i) and (ii) further comprises choline, or salts or esters thereof.

Preferably the composition comprising (i) and (ii) further comprises minerals, preferably magnesium, zinc, manganese and/or molybdenum, more preferably magnesium and/or zinc, more preferably 20-50 mg magnesium, and/or 1-5 mg zinc, even more preferably 25 mg magnesium, and/or 1.5 mg zinc.

Preferably the composition comprising (i) and (ii) further comprises one or more of: phospholipids, vitamin E, vitamin C, selenium, vitamin B12, vitamin B6 and folic acid.

More preferably the composition comprises a uridine source (preferably UMP), DHA, EPA, phospholipids, choline, vitamin E, vitamin C, selenium, vitamin B12, vitamin B6 and folic acid.

More preferably the composition comprises a uridine source (preferably UMP), DHA, EPA, phospholipids, choline, vitamin E, vitamin C, selenium, vitamin B12, vitamin B6, folic acid, magnesium and zinc.

DHA/EPA

In a preferred embodiment, the composition further comprises at least one ω-3 polyunsaturated fatty acid (LC-PUFA; having a chain length of 18 and more carbon atoms) selected from the group consisting of docosahexaenoic acid (22:6; DHA), eicosapentaenoic acid (20:5; EPA) and docosapentaenoic acid (22:5 ω-3; DPA), preferably at least one of DHA and EPA. Preferably the present composition contains at least DHA, more preferably DHA and EPA. EPA is converted to DPA (ω-3), increasing subsequent conversion of DPA to DHA in the brain. Hence, the present composition preferably contains a significant amount of EPA, so to further stimulate in vivo DHA formation.

The DHA, EPA and/or DPA are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

In terms of daily dosage, the present method preferably comprises the administration of 400 to 5000 mg DHA+EPA+DPA (preferably DHA+EPA) per day, more preferably 500 to 3000 mg (preferably DHA+EPA) per day, most preferably 1000 to 2500 mg (preferably DHA+EPA) per day. DHA is preferably administered in an amount of 300 to 4000 mg per day, more preferably 500 to 2500 mg per day.

The present composition preferably comprises 1-40 wt. % DHA, preferably 3-36 wt. % DHA, more preferably 10-30 wt. % DHA, based on total weight of fatty acids. The present composition preferably comprises 0.5-20 wt. % EPA, preferably 2-10 wt. % EPA, more preferably 5-10 wt. % EPA, based on total weight of fatty acids. The above-mentioned amounts take into account and optimize several aspects, including taste (e.g. too high LCP levels reduce taste, resulting in a reduced compliance).

The present composition preferably contains at least one oil selected from fish oil, algae oil and eggs lipids. Preferably the present composition contains fish oil comprising DHA and EPA.

The ratio of the weights of DHA to EPA is preferably larger than 1, more preferably 2:1 to 10:1, more preferably 3:1 to 8:1. The above-mentioned ratios and amounts take into account and optimize several aspects, including taste (too high LCP levels reduce taste, resulting in a reduced compliance), balance between DHA and precursors thereof to ensure optimal effectiveness while maintaining low-volume formulations.

Sources of DHA possible sources of DHA: tuna oil, (other) fish oils, DHA rich alkyl esters, algae oil, egg yolk, or phospholipids enriched with n-3 LCPUFA e.g. phosphatidylserine-DHA.

The present composition preferably contains a very low amount of arachidonic acid (AA). Preferably the weight ratio DHA/AA in the present composition is at least 5, preferably at least 10, more preferably at least 15, preferably up to e.g. 30 or even up to 60. The present method preferably comprises the administration of a composition comprising less than 5 wt. % arachidonic acid based on total fatty acids, more preferably below 2.5 wt. %, e.g. down to 0.5 wt %.

ALA/LA

It is preferred that the alpha-linolenic acid [ALA] content of the composition is maintained at low levels. The ALA concentration may preferably be maintained at levels less than 2.0 wt. %, more preferably below 1.5 wt. %, particularly below 1.0 wt. %, calculated on the total weight of all fatty acids.

Linoleic acid [LA] concentrations can be maintained at normal levels, i.e. between 20 to 30 wt. %, although in one embodiment the LA concentration is also significantly reduced to an amount of <15 g/100 g fatty acids and even less than 10 wt. %. The LA concentrations are preferably at least 1 wt. % based on the total weight of the fatty acids.

The weight ratio omega-6/omega-3 fatty acids in the present product is preferably below 0.5, more preferably below 0.2, e.g. down to 0.05 or to 0.01. The ratio ω-6/ω-3 fatty acids (C20 and higher) in the present product is preferably below 0.3, more preferably below 0.15, e.g. down to 0.06 or to 0.03.

Saturated and Monounsaturated Fatty Acids

The present composition preferably comprises saturated and/or mono-unsaturated fatty acids. The amount of saturated fatty acids is preferably 6-60 wt. % based on total weight of fatty acids, preferably 12-40 wt. %, more preferably 20-40 wt. % based on total weight of fatty acids. In particular the amount of C14:0 (myristic acid)+C16:0 (palmitic acid) is preferably 5-50 wt. %, preferably 8-36 wt. %, more preferably 15-30 wt. %, based on total weight of fatty acids. The total amount of monounsaturated fatty acids, such as oleic acid and palmitoleic acid, is preferably between 5 and 40 wt. %, more preferably between 15 and 30 wt. %, based on total weight of fatty acids. A composition with these preferred amounts was found to be very effective.

Choline

In a preferred embodiment, the present composition contains choline, a choline salt and/or choline ester. For the remainder of the paragraph, the term 'choline' shall be considered to encompass all these equivalents. The choline salt is preferably selected from choline chloride, choline bitartrate, or choline stearate. The choline ester is preferably selected from a phosphatidylcholine and lyso-phosphatidylcholine. The present method preferably comprises the administration of more than 50 mg choline per day, preferably 80 to 2000 mg choline per day, more preferably 120 to 1000 mg choline per day, most preferably 150 to 600 mg choline per day. The present composition preferably comprises 50 mg to 3000 gram choline per 100 ml of the liquid composition, preferably 200 mg to 1000 mg choline per 100 ml. The above numbers are based on choline, the amounts of choline equivalents or sources can be calculated taking the molar equivalent to choline into account.

Phospholipids

Preferably, the present composition preferably comprises phospholipids, preferably 0.1-50 wt. % phospholipids based on total weight of lipids, more preferably 0.5-20 wt. %, more preferably between 1 and 10 wt. %, most preferably between 1 and 5 wt. % based on total weight of lipids. The total amount of lipids is preferably between 10 and 30 wt. % on dry matter, and/or between 2 and 10 g lipid per 100 ml for a liquid composition. The composition preferably comprises between 0.01 and 1 gram lecithin per 100 ml, more preferably between 0.05 and 0.5 gram lecithin per 100 ml. A composition with these preferred amounts was found to be very effective. In one embodiment, the phospholipids comprise at least two phospholipids selected from the group consisting of phosphatidylcholine, phosphatidylethanolamine, phosphatidylinositol and phosphatidylserine, preferably at least PC and PE.

Vitamins

The present combination preferably comprises at least one B vitamin. The vitamin B is selected from the group of vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid or folate), and vitamin B12 (various cobalamins). Functional equivalents are encompassed within these terms.

Preferably, at least one vitamin B is selected from the group of vitamin B6, vitamin B12 and vitamin B9. Preferably the present composition comprises at least two selected from the group consisting of vitamin B6, vitamin B12 and vitamin B9. In particular, good results have been achieved with a combination comprising vitamin B6, vitamin B12 and vitamin B9. Again, functional equivalents are encompassed within these terms.

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (TOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose preferably does not exceed the tolerable upper intake levels (UL), as recommended by IOM.

If present in the nutritional composition or medicament, the vitamin B6 is usually present in an amount to provide a daily dosage in the range of 0.1 to 100 mg, in particular in the range of 0.5 to 25 mg, more in particular in the range of 0.5 to 5 mg. The present composition preferably comprises 0.1 to 100 mg vitamin B6 per 100 g (liquid) product, more preferably 0.5 to 5 mg vitamin B6 per 100 g (liquid) product, more preferably 0.5 to 5 mg vitamin B6 per 100 g (liquid) product.

If present in the nutritional composition or medicament, the vitamin B12 is usually present in an amount to provide a daily dosage in the range of 0.5 to 15 µg, in particular in the range of 1 to 10 µg, more in particular in the range of 1.5 to 5 µg. The present composition preferably comprises 0.5-15 µg vitamin B12 per 100 g (liquid) product, more preferably 1 to 10 µg vitamin B12 per 100 g (liquid) product, more preferably 1.5 to 5 µg vitamin B12 per 100 g (liquid) product. The term "vitamin B12" incorporates all cobalbumin equivalents known in the art.

Throughout the application, the terms 'folic acid', 'folate' and 'B9' are used interchangeably. If present in the nutritional composition or medicament, the vitamin B9 is usually present in an amount to provide a daily dosage in the range of 50 to 1000 µg, in particular in the range of 150 to 750 µg, more in particular in the range of 200 to 500 µg. The present composition preferably comprises 50 to 1000 µg folic acid per 100 g (liquid) product, more preferably 150 to 750 µg folic acid per 100 g (liquid) product, more preferably 200 to 500 µg folic acid per 100 g (liquid) product. Folates include folic acid, folinic acid, methylated, methenylated and formylated forms of folates, their salts or esters, as well as their derivatives with one or more glutamic acid, and all in either reduced or oxidized form.

Vitamins C, E

Vitamin C, or a functional equivalent thereof, may be present in an amount to provide a daily dosage in the range of 20 to 2000 mg, in particular in the range of 30 to 500 mg, more in particular in the range of 75 to 150 mg. In one embodiment, vitamin C, or a functional equivalent thereof, is present in an amount in the range of 20 to 2000 mg, in particular in the range of 30 to 500 mg, more in particular in the range of 75 to 150 mg per 100 ml of the composition.

Tocopherol and/or an equivalent thereof (i.e. a compound having vitamin E activity) may be present in an amount to provide a daily dosage in the range of 10 to 300 mg, in particular in the range of 30 to 200 mg, more in particular in the range of 35 to 100 mg, to prevent oxidative damage resulting from dietary PUFA. In one embodiment, tocopherol and/or equivalent is present in an amount in the range of 10 to 300 mg, in particular in the range of 30 to 200 mg, more in particular in the range of 35 to 100 mg per 100 ml of the composition. The term "tocopherol and/or an equivalent thereof", and 'alpha-TE', as used in this description, comprises tocopherols, tocotrienols, pharmaceutical and/or nutritional acceptable derivatives thereof and any combination thereof. The above numbers are based on tocopherol equivalents, recognized in the art.

Selenium

The present composition preferably contains selenium, because of its antioxidant activity. Preferably the present method provides the administration of a composition comprising 0.01 and 5 mg selenium per 100 ml liquid product, preferably 0.02 and 0.1 mg selenium per 100 ml liquid product. The amount of selenium administered per day is preferably more than 0.01 mg, more preferably 0.01 to 0.5 mg.

Minerals

The inclusion of suitable sources of magnesium and/or zinc is preferred in order to increase concentrations in tissues like blood, liver and brain. This improves uridine homeostasis and peripheral uridine metabolism, as can be observed by the increased uridine concentrations after an overnight fasting.

Suitable sources of magnesium and zinc include food grade ingredients that allow ample release of the cations in the digestive tract. This ensures a high bioavailability of magnesium and zinc. Examples of such ingredients are salts of the cations with organic acids as known in the art and salts with inorganic anions like bicarbonate, sulphate, nitrate, hydoxide, and chloride as known in the art.

The recommended daily dosages which are needed for efficacy are for magnesium 18-60 mg, preferably 20 to 52 mg, most preferably 24 to 48 mg and for zinc 1.1 to 9.0 mg, preferably 1.3 to 6 mg, most preferably 1.4 to 4.8 mg.

Protein

Although the composition may further comprise proteinaceous material, it has been found that such component is not deemed necessary. In fact, it is thus possible to concentrate the actives in a low volume composition. Should a protein fraction be included, the protein fraction comprises intact proteins, peptides as may be obtained by hydrolyses of intact proteins and by syntheses, derivatives of peptides comprising more than 80 wt. % amino acids. Nitrogen from nucleosides material and choline will not be calculated as being protein.

In one embodiment, it is preferred that the composition has a protein content of less than 15 en %, more preferably less than 10 en %, most preferably less than 5 en % of the total energy content of the composition. The energy percentages of the components are calculated using the calculation factors 9 kcal per g lipid, 4 kcal per g protein or g digestible carbohydrates, 2 kcal per g dietary fibers and zero kcal for the other components in the composition. In one embodiment, it is preferred that the composition comprises less than 0.5 to 10 g protein per 100 ml, more preferably less than 1 to 6 gram protein per 100 ml, most preferably 2 to 6 gram protein/100 ml.

A preferred composition according to the invention comprises, per daily dose or per 100 ml composition:
  an amount of a uridine source as described above, said uridine source being preferably UMP;
  100-500 mg, preferably 200-400 mg EPA,
  900-1500 mg, preferably 950-1300 mg DHA,
  50-600 mg, preferably 60-200 mg phospholipids,
  200-600 mg, preferably 300-500 mg choline,
  20-60 mg, preferably 30-50 mg vitamin E (alpha-TE),
  60-100 mg, preferably 60-90 mg vitamin C,
  40-80 µg, preferably 45-65 µg selenium,
  1-5 µg, preferably 2-4 µg vitamin B12,
  0.5-3 mg, preferably 0.5-2 mg vitamin B6, and
  200-600 µg, preferably 300-500 µg folic acid.

More preferred, a composition according to the invention comprises per 100 ml composition:
  an amount of UMP (uridine monophosphate) as described above,
  100-500 mg, preferably 200-400 mg EPA,
  900-1500 mg, preferably 950-1300 mg DHA,
  50-600 mg, preferably 60-200 mg phospholipids,
  200-600 mg, preferably 300-500 mg choline,
  20-60 mg, preferably 30-50 mg vitamin E (alpha-TE),
  60-100 mg, preferably 60-90 mg vitamin C,
  40-80 µg, preferably 45-65 µg selenium,
  1-5 µg, preferably 2-4 µg vitamin B12,
  0.5-3 mg, preferably 0.5-2 mg vitamin B6, and
  200-600 µg, preferably 300-500 µg folic acid.

The compositions as described above can be used as a nutritional therapy, nutritional support, as a medical food, as a food for special medical purposes or as a nutritional supplement. Such product can be consumed at one, two or three servings between 75 and 200 ml per day or per unit, most preferably between 90 and 150 ml/day, most preferably about 125 mL per day in the aforementioned applications.

The subjects that can benefit from the method and composition of the invention often experience problems with eating. Their sensory capabilities and/or control of muscles can become imparted, as well as in some instances their ambition to apply proper eating habits. Swallowing and/or mastication may be problematic. Hence, the present composition is preferably provided in the form of a drink capable of being ingested through a straw.

Related therewith, the composition according to the invention preferably has a low viscosity, preferably a viscosity between 1 and 2000 mPa·s measured at a shear rate of 100 sec-1 at 20° C., more preferably a viscosity between 1 and 100 mPa·s measured at a shear rate of 100 sec-1 at 20° C. In a preferred embodiment the present composition has a viscosity of 1-80 mPa·s at a shear rate of 100 per sec at 20° C., more preferably of 1-40 mPa·s at a shear rate of 100 per sec at 20° C. These viscosity measurements may for instance be performed using plate and cone geometry.

To be optimally accepted by the subject, the present composition preferably has an osmolality of 300 to 800 mOsm/kg. However, the energy density of the product is preferably not so high that it interferes with normal eating habits. When in liquid form, the present product preferably contains between 0.2 and 3 kcal/ml, more preferably between 0.5 and 2, between 0.7 and 1.5 kcal/ml.

EXAMPLES

Example 1: Uridine Homeostasis

The inventors have found that all of these goals were achieved in clinical trials wherein a composition comprising 625 mg uridine monophosphate (UMP) was administered once a day for a period of 24 weeks to people above 60 years. Plasma uridine concentrations were measured about 24 hours after the intake of said composition, and after a period in which no significant uridine source was administered to the subject (i.e. no more than in a normal diet, i.e. less than 100 mg, even less than 50 mg for a normal diet over 24 h). Based on the knowledge on pharmacokinetic properties of UMP existing in the art, one would have expected that all orally administered UMP and its metabolites, in particular uridine, would have been cleared from the plasma long before the measurements occurred. On the contrary, it was surprisingly observed that uridine plasma concentrations after fasting were normalized.

Strikingly, the inventors found that after the initial dosage regimen of administering an uridine source daily, uridine plasma levels were maintained within physiologically acceptable levels, i.e. between 4 and 8 µM, preferably between 4.5-7 µM, more preferably between 4.5-6 µM, for a prolonged period of time, in particular for more than 2, 3, 4 or 5 days, more particularly for at least one week, even when the daily administration of a uridine source was (significantly) reduced, or even stopped over said period of time.

Example 2: Packaged Composition for Comprising Per 125 ml

Energy 125 kcal; Protein 3.9 g; Carbohydrate 16.5 g; Fat 4.9 g.

Fat includes 1.5 g DHA+EPA, and 106 mg phospholipids (soy lecithin); Choline 400 mg; UMP (uridine monophosphate) 625 mg; Vitamin E 40 mg alpha-TE; Vitamin C 80 mg; Selenium 60 µg; Vitamin B12 3 µg; Vitamin B6 1 mg; Folic acid 400 µg.

Minerals and trace elements: Sodium 125 mg; Potassium 187.5 mg; Chloride 156.3 mg; Calcium 100 mg; Phosphorus 87.5 mg; Magnesium 25 mg; Iron 2 mg; Zinc 1.5 mg; Copper 225 µg; Manganese 0.41 mg; Molybdenum 12.5 µg; Chromium 8.4 µg; Iodine 16.3 µg. Vitamins: Vit. A 200 µg-RE; vit. D3 0.9 µg; vit. K 6.6 µg; Thiamin (B1) 0.19 mg;

Riboflavin (B2) 0.2 mg; Niacin (B3) 2.25 mg-NE; Pantothenic acid (B5) 0.66 mg; Biotin 5 µg.

Example 3. Clinical Study

A proof-of-concept study in drug-naïve patients with mild AD (MMSE 20-26) showed that a composition according to the invention (see table 1; comprising DHA, EPA, UMP, choline, phospholipids, vitamins B6, B9, B12, vitamins C and E, Selenium) taken once per day was safe and yielded uridine plasma concentrations within physiologically acceptable ranges in a subject after 24 weeks

TABLE 1

Nutritional composition used in clinical trials

| component | Amount per daily dose |
|---|---|
| EPA | 300 mg |
| DHA | 1200 mg |
| Phospholipids | 106 mg |
| Choline | 400 mg |
| UMP | 625 mg |
| Vitamin E (alpha-TE) | 40 mg |
| Vitamin C | 80 mg |
| Selenium | 60 µg (mcg) |
| Vitamin B12 | 3 µg (mcg) |
| Vitamin B6 | 1 mg |
| Folic acid | 400 µg (mcg) |

*125 ml, daily dose.

Material and Methods

The study was a randomized, controlled, double-blind study, conducted at 29 study centers in the Netherlands, Germany, Belgium, UK and US). Drug-naïve patients with mild AD (MMSE scores 20-26) and diagnosis of probable AD according to the NINCDS-ADRDA criteria, were randomly assigned (1:1) to the composition including the components according to table 1, or an iso-caloric control product. The duration of intervention was 24 weeks.

Plasma samples were taken in overnight fasted patients, at 24 weeks, approximately 24 hours after the last consumption of the placebo or the composition comprising said uridine source. The placebo or control product lacked the constituents as listed in table 1, but was otherwise isocaloric, isonitrogenic, similar in flavour and appearance to the active product, and presented in identical format.

Perchloric acid was added to the plasma sample. Uridine/Uracil/Cytidine were extracted by vortexing of the solution. Reversed-phase HPLC was used to separate components from other nucleotides/nucleosides. The absorbance of the compound at 260 (and 210 nm) compared to a standard, was used for quantification.

Example 4. First and Second Dosage Regimen

Subjects in need thereof receive a product according to example 3 for 12 weeks. After this period the subjects can continue with a second composition which comprises half the dose of uridine in a 60 ml shot format, which is further comprising all macro- and micronutrients and is having an energy density between 1.0 and 1.8 kcal per ml.

The invention claimed is:

1. A method for increasing, controlling and/or maintaining fasting plasma uridine concentrations in a range of 4 to 8 µM in a human subject in need thereof, the method comprising:
    (a) administering daily to the human subject a first composition comprising 300-900 mg of a uridine source for a period of at least 4 weeks, wherein the uridine source comprises at least one of uridine, salts of uridine, phosphates of uridine, acyl derivatives of uridine and/or esters of uridine; and, subsequently,
    (b) administering a second composition comprising a uridine source, wherein the uridine source comprises at least one of uridine, salts of uridine, phosphates of uridine, acyl derivatives of uridine and/or esters of uridine,
    wherein the second composition comprises at least 25-90% less uridine than the first composition.

2. The method according to claim 1, wherein the composition further comprises a lipid fraction comprising at least one of docosahexaenoic acid (22:6; DHA), eicosapentaenoic acid (20:5; EPA), docosapentaenoic acid (22:5; DPA), and esters thereof.

3. The method according to claim 1, wherein the composition further comprises folic acid.

4. The method according to claim 3, wherein the composition comprises 50-500 µg folic acid per daily dose or per 100 ml composition.

5. The method according to claim 1, wherein the composition further comprises choline, or salts or esters thereof.

6. The method according to claim 5, wherein the composition comprises 200-600 mg choline per daily dose or per 100 ml composition.

7. The method according to claim 1, wherein the composition further comprises at least one B vitamin selected from the group consisting of vitamin B6, vitamin B12 and vitamin B9.

8. The method according to claim 1, wherein the composition further comprises phospholipids.

9. The method according to claim 1, wherein the composition further comprises minerals.

10. The method according to claim 9, wherein the minerals comprise magnesium and/or zinc.

11. The method according to claim 1, wherein the composition comprises, per daily dose or per 100 ml composition:
    (a) 50-1000 mg phospholipids,
    (b) 0.5-3 mg vitamin B6,
    (c) 50-500 µs folic acid,
    (d) 1-30 µg vitamin B12.

12. The method according to claim 1, wherein the composition is administered for a period ranging from 4 to 52 weeks.

13. The method according to claim 1, wherein the composition is administered once daily.

14. The method according to claim 1, wherein the subject is elderly.

15. The method according to claim 1, wherein the subject suffers from a pathological brain dysfunction, as can be determined by applying functional tests for measuring the different domains of brain function.

16. The method according to claim 1, wherein the subject suffers from or is at risk of a neurodegenerative disorder.

17. The method according to claim 1, wherein the subject suffers from or is at risk of a memory or cognitive disorder, memory decline or cognitive dysfunction.

18. The method according to claim 1, wherein said the subject suffers from or is at risk of Age Associated Memory Impairment (AAMI); Alzheimer's Disease; Parkinson; Pick's disease; dementia, vascular dementia, frontotemporal dementia, semantic dementia or dementia with Lewy bodies, and/or Mild Cognitive Impairment (MCI).

19. The method according to claim 18, wherein the subject suffers from or is at risk of Alzheimer's disease.

20. The method according to claim 1, wherein the first composition comprises 500-900 mg of the uridine source.

21. The method according to claim 1, wherein the administration does not result in increased renal clearance of uridine.

22. The method according to claim 1, wherein the second composition comprises 50-90% less uridine than the first composition.

23. The method according to claim 22, wherein the second composition comprises 50-75% less uridine than the first composition.

24. The method according to claim 1, wherein the fasting plasma uridine concentration is determined after 9 to 24 hours following administration of the first or second composition.

25. The method according to claim 1, wherein the fasting plasma uridine concentration is determined after at least 9 hours following administration of the first or second composition.

* * * * *